United States Patent
Kaneda

(10) Patent No.: US 10,435,724 B2
(45) Date of Patent: Oct. 8, 2019

(54) METHOD FOR PRODUCING C4 DICARBOXYLIC ACID

(71) Applicant: Kao Corporation, Chuo-ku, Tokyo (JP)

(72) Inventor: Jitsuro Kaneda, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 15/767,424

(22) PCT Filed: Oct. 12, 2016

(86) PCT No.: PCT/JP2016/080234
§ 371 (c)(1),
(2) Date: Apr. 11, 2018

(87) PCT Pub. No.: WO2017/065167
PCT Pub. Date: Apr. 20, 2017

(65) Prior Publication Data
US 2018/0291406 A1    Oct. 11, 2018

(30) Foreign Application Priority Data
Oct. 13, 2015  (JP) ................................. 2015-201959

(51) Int. Cl.
*C12P 7/46* (2006.01)
*C12N 1/20* (2006.01)
*C12N 15/00* (2006.01)
*C07H 21/04* (2006.01)
*C07K 1/00* (2006.01)
*C07K 14/37* (2006.01)
*C12N 15/80* (2006.01)

(52) U.S. Cl.
CPC ............... *C12P 7/46* (2013.01); *C07K 14/37* (2013.01); *C12N 15/80* (2013.01)

(58) Field of Classification Search
None
See application file for complete search history.

(56) References Cited

U.S. PATENT DOCUMENTS

| 5,436,158 | A * | 7/1995 | Takagi | ................... | C12N 15/80 435/254.9 |
|---|---|---|---|---|---|
| 2011/0312046 | A1 | 12/2011 | Luttringer et al. | | |
| 2018/0327791 | A1 | 11/2018 | Kaneda | | |

FOREIGN PATENT DOCUMENTS

| CN | 103013843 A | 4/2013 |
|---|---|---|
| JP | 46-028828 B | 8/1971 |
| JP | 2013-230142 A | 11/2013 |
| WO | WO 2017/073640 A1 | 5/2017 |

OTHER PUBLICATIONS

Studer. Residue mutations and their impact on protein structure and function: detecting beneficial and pathogenic changes. Biochem. J. (2013) 449, 581-594.*

Ma Genomic analysis of the basal lineage fungus Rhizopus oryzae reveals a whole-genome duplication. PLoS Genet. 5:E1000549-E1000549 (2009).*

International Search Report (ISR) for PCT/JP2016/080234; I.A. fd Oct. 12, 2016, dated Dec. 13, 2016 from the Japan Patent Office, Tokyo, Japan.

International Preliminary Report on Patentability (IPRP), Chapter I of the Patent Cooperation Treaty, including the Written Opinion for PCT/JP2016/080234; I.A. fd Oct. 12, 2016, dated Apr. 17, 2018, by the International Bureau of WIPO, Geneva, Switzerland.

Zhang, B. et al., "Metabolic engineering of *Rhizopus oryzae*: Effects of overexpressing pyc and pepc genes on fumaric acid biosynthesis from glucose," Metab Eng. Sep. 2012;14(5):512-20. doi: 10.1016/j.ymben.2012.07.001. Epub Jul. 17, 2012, Academic Press, Orlando, FL.

Lang, B.F. et al., Accession: EE007951, Definition: ROE00001593 Rhizopus oryzae Company Rhizopus oryzae cDNA, mRNA sequence, DDBJ [online], entire text, Jul. 18, 2006, <URL: http://getentry.ddbj.nig.acjp/getentry/na/EE007951/?format=flatfile&filetype=html&trace=true&show_suppressed=false&limit=10> [retrieved on Nov. 2, 2016].

Ma, L.J. et al., Accession: I1CFF2, Definition: Uncharacterized protein, UNIPROT [online], entire text, Jun. 13, 2012, <url: http://www.uniprot.org/uniprot/I1CFF2.txt?version=1> [retrieved on Nov. 2, 2016].

* cited by examiner

*Primary Examiner* — Yong D Pak
(74) *Attorney, Agent, or Firm* — Sterne, Kessler, Goldstein & Fox P.L.L.C.

(57) ABSTRACT

Improvement of C4 dicarboxylic acid productivity in a host cell. A polypeptide consisting of an amino acid sequence represented by SEQ ID No: 2 or an amino acid sequence having an identity of at least 90% with the amino acid sequence represented by SEQ ID No: 2.

25 Claims, No Drawings

Specification includes a Sequence Listing.

METHOD FOR PRODUCING C4 DICARBOXYLIC ACID

FIELD OF THE INVENTION

The present invention relates to a biological production of a C4 dicarboxylic acid.

BACKGROUND OF THE INVENTION

C4 dicarboxylic acids are used not only for various applications in the food industry, as an acidulant, an antimicrobial agent and a pH modifier, but also as a raw material for synthetic resins and biodegradable polymers, and are industrially valuable substances. Industrially, C4 dicarboxylic acids are produced by either chemical synthesis from petrochemical raw materials or microbial fermentation. Conventionally, a chemical synthesis method has been dominantly used because its lower cost; however, recently, in view of e.g., a sharp increase in material cost and environmental load, the production method by microbial fermentation using a recyclable resource as a raw material has attracted attention.

Fumaric acid, one of the C4 dicarboxylic acids, is known to be produced using a fermentative bacterium such as *Rhizopus*. *Rhizopus* utilizes glucose as a carbon source to produce fumaric acid and excretes it to the outside the cell. To date, regarding techniques for increasing production of fumaric acid by *Rhizopus*, for example, improvement in a culture method and preparation of a highly productive strain by mutation breeding are known. However, genetic background of *Rhizopus* has not yet been sufficiently studied and thus, it is not easy to develop a technology for improved production of a fumaric acid by *Rhizopus* through genetic recombination, and the number of reports is few. It is only reported that fumaric acid productivity is improved by introducing a gene encoding pyruvate carboxylase and derived from *Saccharomyces cerevisiae*, in *Rhizopus delemar* (Patent Literature 1); and introducing a gene encoding phosphoenolpyruvate carboxylase and derived from *Escherichia coli* in *Rhizopus oryzae* (Non Patent Literature 1).

(Patent Literature 1) Chinese Patent Publication No. CN103013843

(Non Patent Literature 1) Metabolic Engineering, 2012, 14: 512-520

SUMMARY OF THE INVENTION

The present invention provides a polypeptide consisting of an amino acid sequence represented by SEQ ID No: 2 or an amino acid sequence having an identity of at least 90% with the amino acid sequence represented by SEQ ID No: 2.

The present invention provides a polynucleotide encoding the polypeptide mentioned above.

The present invention provides a vector comprising the polynucleotide mentioned above.

The present invention provides a transformed cell comprising the polynucleotide or vector mentioned above.

The present invention provides a method for producing a C4 dicarboxylic acid, comprising culturing the transformed cell mentioned above.

The present invention provides a method for producing a transformed cell, comprising introducing the polynucleotide or vector mentioned above into a host cell.

The present invention further provides a method for improving C4 dicarboxylic acid productivity in a host cell, comprising introducing the polynucleotide or vector mentioned above into a host cell.

DETAILED DESCRIPTION OF THE INVENTION

The present invention relates to a polypeptide having an effect of improving C4 dicarboxylic acid productivity on a host cell, a gene encoding the polypeptide, a transformed cell containing the gene and a method for producing a C4 dicarboxylic acid using the transformed cell.

As a result of intensive studies, the present inventor found that when expression of a polypeptide consisting of the amino acid sequence represented by SEQ ID No: 2 is enhanced in a cell, C4 dicarboxylic acid productivity in the cell can be improved.

The polypeptide of the present invention has a function to improve C4 dicarboxylic acid productivity in a cell. A cell in which expression of the polypeptide of the present invention is enhanced (for example, a cell in which a gene encoding the polypeptide is introduced) can produce a larger amount of a C4 dicarboxylic acid. Accordingly, the polypeptide of the present invention and the cell enhanced in expression of the polypeptide are useful for biological production of a C4 dicarboxylic acid. The features and advantages of the present invention mentioned above (including those not mentioned above) will be more clearly understood based on the following description of the specification.

1. Definition

In the specification, an identity of amino acid sequences or nucleotide sequences can be calculated in accordance with the Lipman-Pearson method (Science, 1985, 227: 1435-1441). More specifically, the identity can be analyzed based on the homology analysis program of genetic information processing software GENETYCS Ver. 12 (i.e., amino acid sequence×amino acid sequence maximum matching or nucleotide sequence×nucleotide sequence maximum matching) and by assigning −1 to Maches, 1 to Mismatches, 1 to Gaps and *N+2.

In the specification, "an identity of at least 90%" regarding an amino acid sequence or a nucleotide sequence refers to an identity of 90% or more, preferably 95% or more, more preferably 96% or more, further preferably 97% or more, still further preferably 98% or more and further more preferably 99% or more.

In the specification, "the corresponding region" of an amino acid sequence or a nucleotide sequence can be determined by aligning a sequence of interest and a reference sequence (for example, the amino acid sequence represented by SEQ ID No: 2) so as to obtain a maximum homology. Amino acid sequences or nucleotide sequences can be aligned by use of an algorithm known in the art and the procedure thereof is known to those skilled in the art. For example, the alignment can be manually made based on e.g., the Lipman-Pearson method mentioned above, or alternatively, based on Clustal W multiple alignment program (Thompson, J. D. et al, 1994, Nucleic Acids Res. 22: 4673-4680) by default. Clustal W can be used on the website of, for example, the European Bioinformatics Laboratory (European Bioinformatics Institute: EBI [www.ebi.ac.uk/index.html]) or the DNA Data Bank of Japan (DDBJ[www.ddbj.nig.ac.jp/Welcome-j.html]) managed by the National Institute of Genetics. The region of the sequence of interest aligned with an optional region of a reference sequence by the alignment operation is regarded as "the corresponding region" to the optional region.

In the specification, the "amino acid sequence having deletion, substitution, addition or insertion of one or a plurality of amino acids" refers to an amino acid sequence having deletion, substitution, addition or insertion of 1 or more and 10 or less, preferably 1 or more and 8 or less, more preferably 1 or more and 5 or less and further preferably 1 or more and 3 or less amino acid(s). In the specification, the "nucleotide sequence having deletion, substitution, addition or insertion of one or a plurality of nucleotides" refers to a nucleotide sequence having deletion, substitution, addition or insertion of 1 or more and 30 or less, preferably 1 or more and 24 or less, more preferably 1 or more and 15 or less and still further preferably 1 or more and 9 or less nucleotide(s). In the specification, "addition" of an amino acid or a nucleotide includes addition of the amino acid or the nucleotide to one and both ends of a sequence.

In the specification, "upstream" and "downstream" regarding a gene refer to upstream and downstream of the gene in the transcriptional orientation. For example, "a gene arranged downstream of a promoter" means that the gene is present on the 3' side of the promoter in a DNA sense strand and the upstream of a gene means the region on the 5' side of the gene in the DNA sense strand.

In the specification, the "operable linking" between a regulatory region and a gene refers to the linking of the gene to the regulatory region such that the gene can be expressed under control of the regulatory region. A procedure for "operable linking" between a gene and a regulatory region is well known to those skilled in the art.

In the specification, the term "intrinsic" used for function, property and trait of a cell means that the function, property and trait are present in the cell of a wild type. In contrast, the term "exogenous" is used for representing that the function, property and trait are not originally present in the cell but externally introduced in the cell. For example, an "exogenous" gene or polynucleotide is a gene or polynucleotide introduced in a cell from the outside. The exogenous gene or polynucleotide may be derived from a homogeneous biological species of the cell in which the gene or polynucleotide is introduced or a different biological species (more specifically, heterologous gene or polynucleotide).

In the specification, "C4 dicarboxylic acid productivity" of a cell is represented as a yield (%) of a C4 dicarboxylic acid in a culture medium of the cell; more specifically, mass (%) of an amount of the C4 dicarboxylic acid produced by the cell relative to an amount of a carbon source consumed in the culture medium of the cell. The amount of a C4 dicarboxylic acid produced by a cell can be calculated as the amount of the C4 dicarboxylic acid in the culture supernatant, which is obtained by removing cells from a cultured broth of the cells. The amount of a carbon source consumed in the culture medium can be calculated by subtracting the amount of a carbon source in the culture supernatant from the initial concentration of the carbon source in the culture medium. The amounts of a C4 dicarboxylic acid and carbon source in the culture supernatant can be measured by e.g., high-speed liquid chromatography (HPLC). The measurement procedure will be more specifically described later in Reference Example 1.

In the specification, "improvement of C4 dicarboxylic acid productivity" in a transformed cell means that C4 dicarboxylic acid productivity of the transformed cell is improved compared to that of a host cell or a control cell. The improvement rate of C4 dicarboxylic acid productivity in a transformed cell is calculated in accordance with the following expression:

$$\text{Improvement rate (\%)} = (\text{C4 dicarboxylic acid productivity in a transformed cell}/\text{C4 dicarboxylic acid productivity of host cell or control cell}) \times 100 - 100$$

The transformed cell herein refers to a cell enhanced in expression of the polypeptide of the present invention, for example, a cell in which a polynucleotide encoding the polypeptide of the present invention or a vector containing the polynucleotide is introduced. The host cell refers to a host cell (a parent cell) for the transformed cell. The control cell refers to a cell in which a vector not containing a polynucleotide encoding the polypeptide of the present invention is introduced. Preferably, the improvement rate of C4 dicarboxylic acid productivity is calculated based on the C4 dicarboxylic acid productivity of the transformed cell at a maximum time point of C4 dicarboxylic acid concentration in the culture supernatant (containing no cells) of the transformed cell. Accordingly, in the specification, "a transformed cell improved in C4 dicarboxylic acid productivity by X % or more" refers to a transformed cell exhibiting an improvement rate of C4 dicarboxylic acid productivity, calculated in accordance with the above expression, of X % or more. The "improvement of C4 dicarboxylic acid productivity by X % or more" in a cell means that the improvement rate of C4 dicarboxylic acid productivity of the cell, calculated in accordance with the above expression, is X % or more.

Examples of the C4 dicarboxylic acid to be produced by the present invention include fumaric acid, malic acid and succinic acid, and fumaric acid is preferable.

In the specification, a "multiple transmembrane polypeptide" refers to a transmembrane polypeptide predicted to have a plurality of transmembrane helix structures based on an analysis using a cell transmembrane region prediction program. Examples of the cell transmembrane region prediction program include analysis programs using a prediction method such as TMHMM Server, v. 2.0 (Journal of Molecular Biology, 2001, 305: 567-580), DAS-TMfilter (Protein Eng., 2002, Volume 15, Issue 9: 745-752) and PRED-TMR2 (Protein Eng., 1999, Volume 12, Issue 8: 631-634).

2. Improvement of C4 Dicarboxylic Acid Productivity of Cell (2.1. Novel Polypeptide)

In an embodiment, the present invention provides a polypeptide consisting of the amino acid sequence represented by SEQ ID No: 2 or an amino acid sequence having an identity of at least 90% with the amino acid sequence represented by SEQ ID No: 2.

As a result of an analysis using a cell transmembrane region prediction program, TMHMM Server, v. 2.0, the polypeptide of the present invention consisting of the amino acid sequence represented by SEQ ID No: 2 had a transmembrane helix structure in each of the 24th to 46th, 118th to 140th and 147th to 165th amino acid regions of the amino acid sequence and was predicted as a three transmembrane polypeptide. Accordingly, the polypeptide of the present invention is predicted to be a multiple transmembrane polypeptide. In consideration of the fact that a transporter polypeptide having an activity to transport a substance inside and outside the cell membrane usually has a multiple transmembrane structure, it is predicted that the polypeptide of the present invention is a transporter-like polypeptide. In contrast, as a result of search based on polypeptide database (for example, ncbi's Non-Redundant protein sequences (nr)), a protein (accession number: RO3G_11893), unknown in function and derived from *Rhizopus delemar* RA 99-880, was found as a known protein having the highest identity with the polypeptide of the present invention consisting of the amino acid sequence represented by SEQ ID No: 2. The sequence identity thereof was 88.82%. As a result of the TMHMM analysis, the protein unknown in function was predicted to be a two transmembrane polypeptide having a transmembrane helix structure in each of the 24th to 46th and 118th to 140th amino acid regions of the amino acid sequence, and thus the protein unknown in function was found to be different from the polypeptide of the present invention which is a three transmembrane polypeptide. From the above, it was determined that the polypeptide of the present invention is a novel polypeptide so far not known.

Accordingly, in a preferable embodiment, the polypeptide of the present invention is a multiple transmembrane polypeptide having three transmembrane helix structures and consisting of the amino acid sequence represented by SEQ ID No: 2 or an amino acid sequence having an identity of at least 90% with the amino acid sequence represented by SEQ ID No: 2. In a more preferable embodiment, the polypeptide is a multiple transmembrane polypeptide consisting of an amino acid sequence having an identity of at least 90% with the amino acid sequence represented by SEQ ID No: 2 and having a transmembrane helix structure in each of the corresponding regions to the 24th to 46th, 118th to 140th and 147th to 165th amino acid regions of the amino acid sequence represented by SEQ ID No: 2.

Examples of the amino acid sequence having an identity of at least 90% with the amino acid sequence represented by SEQ ID No: 2 include an amino acid sequence having deletion, substitution, addition or insertion of one or a plurality of amino acids with respect to the amino acid sequence represented by SEQ ID No: 2.

As a method of introducing a mutation such as deletion, substitution, addition or insertion of an amino acid(s) in an amino acid sequence, for example, a method of introducing a mutation such as deletion, substitution, addition or insertion of a nucleotide(s) in the nucleotide sequence encoding the amino acid sequence, is mentioned. Examples of a technique of introducing a mutation in a nucleotide sequence, include mutagenesis with a chemical mutagen such as ethyl methanesulfonate, N-methyl-N-nitrosoguanidine and nitrous acid, or a physical mutagen such as an ultraviolet ray, X ray, gamma ray and an ion beam, a site-specific mutagenesis and a method described by Dieffenbach et al. (Cold Spring Harbar Laboratory Press, New York, 581-621, 1995). Examples of the site-specific mutagenesis method include a method using Splicing overlap extension (SOE) PCR (Horton et al., Gene 77, 61-68, 1989), ODA method (Hashimoto-Gotoh et al., Gene, 152, 271-276, 1995) and Kunkel method (Kunkel, T. A., Proc. Natl. Acad. Sci. USA, 1985, 82, 488). Alternatively, a commercially available kit for site-specific mutagenesis such as Site-Directed Mutagenesis System Mutan-SuperExpress Km kit (Takara Bio Inc.), Transformer™ Site-Directed Mutagenesis kit (Clontech) and KOD-Plus-Mutagenesis Kit (Toyobo Co., Ltd.), can be used.

(2.2. Gene, Vector and Transformed Cell)

In another embodiment, the present invention provides a polynucleotide encoding the polypeptide of the present invention. In a preferable embodiment, as the polynucleotide of the present invention, a polynucleotide consisting of a nucleotide sequence represented by SEQ ID No: 1 and a polynucleotide consisting of a nucleotide sequence having an identity of at least 90% with the nucleotide sequence represented by SEQ ID No: 1 may be mentioned. In a preferable embodiment, the polynucleotide of the present invention encodes a polypeptide consisting of the amino acid sequence represented by SEQ ID No: 2 or a multiple transmembrane polypeptide consisting of an amino acid sequence having an identity of at least 90% with the amino acid sequence represented by SEQ ID No: 2 and having three transmembrane helix structures. In a more preferable embodiment, the polynucleotide of the present invention encodes a polypeptide consisting of the amino acid sequence represented by SEQ ID No: 2 or a multiple transmembrane polypeptide consisting of an amino acid sequence having an identity of at least 90% with the amino acid sequence represented by SEQ ID No: 2 and having a transmembrane helix structure in each of the corresponding regions to the 24th to 46th, 118th to 140th and 147th to 165th amino acid regions of the amino acid sequence represented by SEQ ID No: 2.

Examples of the nucleotide sequence having an identity of at least 90% with the nucleotide sequence represented by SEQ ID No: 1 include a nucleotide sequence having deletion, substitution, addition or insertion of one or a plurality of nucleotides with respect to the nucleotide sequence represented by SEQ ID No: 1. As a method of introducing a mutation such as a deletion, substitution, addition or insertion of a nucleotide(s) in a nucleotide sequence, for example, the same methods mentioned above are employed. The polynucleotide of the present invention may be a single strand or double strand; or either DNA or RNA. The DNA may be cDNA and an artificial DNA such as a chemically synthesized DNA.

The polynucleotide of the present invention may be integrated in a vector. The vector containing the polynucleotide of the present invention is preferably an expression vector. The vector is preferably an expression vector, through which the polynucleotide of the present invention can be introduced in a host cell and the polynucleotide can be expressed in the host cell. The vector preferably contains the polynucleotide of the present invention and a regulatory region operably linked to the polynucleotide. The vector may be a vector capable of extrachromosomally and autonomously proliferating and replicating such as a plasmid, or a vector intrachromosomally integrated.

Examples of the vector include pBluescript II SK (−) (Stratagene), a pUC vector such as pUC18 (Takara Bio Inc.), a pET vector (Takara Bio Inc.), a pGEX vector (GE healthcare), a pCold vector (Takara Bio Inc.), a pHY300PLK (Takara Bio Inc.), pUB110 (Mckenzie, T. et al., 1986, Plasmid 15 (2): 93-103), pBR322 (Takara Bio Inc.), pRS403 (Stratagene), pMW218/219 (Nippon Gene Co., Ltd.), a pRI vector (Takara Bio Inc.), a pBI vector (Clontech) and an IN3 vector (Inplanta Innovations Inc.).

Alternatively, a DNA fragment containing the polynucleotide of the present invention may be constructed. As the DNA fragment, for example, a DNA fragment amplified by PCR and a DNA fragment digested by a restriction enzyme, may be mentioned. The DNA fragment may be an expression cassette containing the polynucleotide of the present invention and a regulatory region operably linked thereto.

The regulatory region to be contained in a vector or a DNA fragment is a sequence for expressing the polynucleotide of the present invention within a host cell to which the vector or DNA fragment is to be introduced, for example, an expression regulatory region such as a promoter and a terminator, and an origin of replication, are mentioned. The type of the regulatory region can be appropriately selected depending upon the type of host cell to which a vector or a DNA fragment is to be introduced. If necessary, the vector or DNA fragment may further have a selection marker such as an antibiotic resistant gene and amino acid synthesis related genes.

The transformed cell of the present invention can be obtained by introducing a vector or DNA fragment containing the polynucleotide of the present invention in a host cell. This is a transformed cell containing a vector or an exogenous DNA fragment containing the polynucleotide of the present invention. Alternatively, in the case where a host cell has a gene encoding the polypeptide of the present invention on the genome thereof, the transformed cell of the present invention can be obtained by modifying the regulatory region of the gene to improve the transcript amount of the gene in the host cell. In the transformed cell of the present invention, the transcript amount of the gene encoding the polypeptide of the present invention compared to the host cell (parent cell) increases preferably to 120% or more, more preferably 150% or more, further preferably 200% or more, still further preferably 250% or more, further more preferably 300% or more, further more preferably 350% or more and further more preferably 400% or more. In the case where a host cell does not have a gene encoding the polypeptide of the present invention and thus, does not express the polypeptide of the present invention, the transformed cell of the present invention includes a cell whose trait is changed such that the gene is transcribed. The transcript amount of gene can be determined based on measurement of mRNA amount by quantification PCR, RNA-Seq analysis using a next generation sequencer, DNA microarray analysis and the like.

As the host cell for the transformed cell, any one of a microbial cell, a plant cell and an animal cell may be used. In view of production efficiency of a C4 dicarboxylic acid, the host cell is preferably a microbial cell. The microbe may be either a prokaryote or a eukaryote. Of these microbes, in view of C4 dicarboxylic acid productivity, a filamentous fungus or a yeast is preferable and a filamentous fungus is more preferable. Examples of the filamentous fungus include all filamentous fungi belonging to subdivisions, *Eumycota* and *Oomycota* (as defined by Hawksworth et al., In, Ainsworth and Bisby's Dictionary of The Fungi, 8th edition, 1995, CAB International, University, Press, Cambridge, UK). A filamentous fungus is generally characterized by a mycelial wall constituted of chitin, cellulose, glucan, chitosan, mannan or another polysaccharide conjugate. Vegetative growth is made by extension of hyphae and carbon is metabolized in absolute aerobic conditions.

Preferable examples of the filamentous fungus to be used as a host cell for the transformed cell of the present invention include filamentous fungi of the genus *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Parasitelia, Penicillium, Phanerochaete, Phiebia, Piromyces, Pleurotus, Rhizopus, Schizophyllum, Talaromyces, Thermoascus, Thielavia, Tolypocladium, Trametes* and *Trichoderma*. Of these, in view of C4 dicarboxylic acid productivity, filamentous fungi of the genus *Rhizopus* such as *Rhizopus delemar, Rhizopus arrhizus, Rhizopus chinensis, Rhizopus nigricans, Rhizopus tonkinensis, Rhizopus tritici* and *Rhizopus oryzae* are preferable; *Rhizopus delemar* and *Rhizopus oryzae* are more preferable; and *Rhizopus delemar* is further preferable.

In introducing a vector or a DNA fragment in the host cell, a general transformation method such as an electroporation method, a transformation method, a transfection method, a conjugation method, a protoplast method, a particle-gun method and an *Agrobacterium* method, can be used.

A transformed cell having a desired vector or DNA fragment introduced therein can be selected by using a selection marker. For example, when the selection marker is an antibiotic resistant gene, the transformed cell having a desired vector or DNA fragment introduced therein can be selected by culturing the cell in the medium containing the antibiotic. When the selection marker is, for example, an amino acid synthesis related gene, the gene may be introduced in an host cell which is the amino acid-auxotrophic. A transformed cell having a desired vector or DNA fragment introduced therein can be selected based on whether the cell is amino acid auxotrophic or not. Alternatively, introduction of a desired vector or DNA fragment can be confirmed by examining the DNA sequence of the transformed cell by e.g., PCR.

(2.3. Improvement of C4 Dicarboxylic Acid Productivity)

A transformed cell containing a vector or an exogenous DNA fragment containing the polynucleotide of the present invention is improved in transcript amount of the polynucleotide and enhanced in expression of the polypeptide of the present invention. Owing to this, the transformed cell is improved in C4 dicarboxylic acid productivity. The C4 dicarboxylic acid productivity of the transformed cell, compared to a host cell (a parent cell) thereof, is improved by preferably 10% or more, more preferably 15% or more, further preferably 20% or more, still further preferably 25% or more and further more preferably 30% or more.

3. Production of a C4 Dicarboxylic Acid

The transformed cell of the present invention is improved in C4 dicarboxylic acid productivity. Accordingly, the present invention also provides a method for producing a C4 dicarboxylic acid, including culturing the transformed cell of the present invention. As the C4 dicarboxylic acid to be produced by the production method of the present invention, fumaric acid, malic acid and succinic acid are mentioned and preferably fumaric acid is mentioned.

Cultivation a transformed cell in the production method of the present invention includes culturing a microbe, a plant, an animal or a cell or tissue thereof containing the transformed cell. The medium and culture conditions for culturing the transformed cell can be appropriately selected depending upon the type of host for the transformed cell. Usually, a medium and culture condition routinely used for a host for the transformed cell can be employed.

For example, when the transformed cell is a filamentous fungus cell, the culture temperature may be, for example, from 10° C. to 50° C., and preferably from 25° C. to 45° C.; the culture period, which is not particularly limited as long as it is the period during which a desired C4 dicarboxylic acid is sufficiently produced, may be, for example, from 1 to 240 hours, preferably from 12 to 120 hours and preferably from 24 to 72 hours. Culture is preferably carried out while stirring or under aeration.

As a medium for culturing a filamentous fungus, a medium routinely used may be used. The medium is preferably a liquid medium and any one of a synthesis medium, a natural medium, and a semisynthetic medium in which a natural component is added to a synthesis medium, may be used. A commercially available medium such as PDB medium (potato dextrose medium, manufactured by e.g., Becton, Dickinson and Company), PDA medium (manufactured by e.g., Becton, Dickinson and Company), LB medium (Luria-Bertani medium, manufactured by e.g., Nihon Pharmaceutical Co., Ltd. (brand name e.g., "DATGO")), NB medium (Nutrient Broth, manufactured by e.g., Becton, Dickinson and Company), SB medium (Sabouraud medium, manufactured by e.g., OXOID Ltd.) and SD medium (Synthetic Dropout Broth; for example, Clontech), can be used. The medium usually contains e.g., a carbon source, a nitrogen source and an inorganic salt; however, each component composition can be appropriately selected.

Now, the composition of a preferable medium for culturing a filamentous fungus will be more specifically described, below. The concentrations of individual components in the medium described below represent initial concentrations thereof (at the time of preparation of a medium or at the time of starting culture).

Examples of the carbon source in a medium as mentioned above include glucose, maltose, starch hydrolysate, fructose, xylose and sucrose. Of them, glucose and fructose are preferable. These sugars can be used alone or in combination of two or more. The concentration of the carbon source in a medium is preferably 1% (w/v) or more and more preferably 5% (w/v) or more; and preferably 40% (w/v) or less and more preferably 30% (w/v) or less. In short, the concentration of the carbon source in a medium is preferably from 1 to 40% (w/v) and more preferably from 5 to 30% (w/v).

Examples of the nitrogen source in a medium include a nitrogen-containing compound such as ammonium sulfate, urea, ammonium nitrate, potassium nitrate and sodium nitrate. The concentration of the nitrogen source in a medium is preferably from 0.001 to 0.5% (w/v) and more preferably from 0.001 to 0.2% (w/v).

The medium can contain e.g., a sulfate, a magnesium salt and a zinc salt. Examples of the sulfate include magnesium sulfate, zinc sulfate, potassium sulfate, sodium sulfate and ammonium sulfate. Examples of the magnesium salt include magnesium sulfate, magnesium nitrate and magnesium chloride. Examples of the zinc salt include zinc sulfate, zinc nitrate and zinc chloride. The concentration of the sulfate in a medium is preferably from 0.01 to 0.5% (w/v) and more preferably from 0.02 to 0.2% (w/v). The concentration of the magnesium salt in a medium is preferably from 0.001 to 0.5% (w/v) and more preferably from 0.01 to 0.1% (w/v). The concentration of the zinc salt in a medium is preferably from 0.001 to 0.05% (w/v) and more preferably from 0.005 to 0.05% (w/v).

The pH (25° C.) of a medium is preferably from 3 to 7 and more preferably from 3.5 to 6. The pH of a medium can be controlled with a base such as calcium hydroxide, sodium hydroxide, calcium carbonate and ammonia or an acid such as a sulfuric acid and hydrochloric acid.

A preferable example of the medium includes a liquid medium containing from 7.5 to 30% of carbon source, from 0.001 to 0.2% of ammonium sulfate, from 0.001 to 0.6% of potassium dihydrogen phosphate, from 0.01 to 0.1% magnesium sulfate heptahydrate, from 0.005 to 0.05% of zinc sulfate heptahydrate and from 3.75 to 20% calcium carbonate (concentrations are all expressed by % (w/v)).

To efficiently produce a C4 dicarboxylic acid using a transformed fungus (a filamentous fungus as a host), production may be carried out in the steps mentioned below. More specifically, a C4 dicarboxylic acid can be efficiently produced by preparing a spore suspension of a transformed cell (step A), culturing the suspension in a culture solution to germinate the spore, thereby preparing a mycelium (step B1), preferably further proliferating the mycelium (step B2), and then culturing the mycelium prepared to produce the C4 dicarboxylic acid (step C). Note that, the cultivation step of a transformed cell in the present invention is not limited to the following steps.

<Step A: Preparation of Spore Suspension>

Spores of a filamentous fungus transformed are inoculated, for example, on a medium such as an inorganic agar medium (composition example: 2% glucose, 0.1% ammonium sulfate, 0.06% potassium dihydrogen phosphate, 0.025% magnesium sulfate heptahydrate, 0.009% zinc sulfate heptahydrate and 1.5% agar (concentrations are all expressed by % (w/v))) and PDA medium, and subjected to stationary culture at from 10 to 40° C., preferably from 27 to 30° C. for from 7 to 10 days to form spores, which are then suspended in e.g., physiological saline to prepare a spore suspension. The spore suspension may or may not contain a mycelium.

<Step B1: Preparation of Mycelium>

The spore suspension obtained in step A is inoculated in a culture solution and cultured to germinate spores, thereby obtaining mycelia. The number of spores of a filamentous fungus to be inoculated in the culture solution is from $1\times10^2$ to $1\times10^8$ spores/mL (culture solution), preferably from $1\times10^2$ to $5\times10^4$ spores/mL (culture solution), more preferably from $5\times10^2$ to $1\times10^4$ spores/mL (culture solution) and further preferably from $1\times10^3$ to $1\times10^4$ spores/mL (culture solution). As the culture solution, a commercially available medium such as PDB medium, LB medium, NB medium, SB medium and SD medium, can be used. In view of germination rate and mycelium growth, a carbon source including a monosaccharide such as glucose and xylose, an oligosaccharide such as sucrose, lactose and maltose, or a polysaccharide such as starch; a biological component such as glycerin and citric acid; a nitrogen source such as ammonium sulfate, urea and amino acid; and other inorganic substances such as various salts including a sodium salt, a potassium salt, a magnesium salt, a zinc salt, an iron salt and a phosphate may be appropriately added to the culture solution. The preferable concentrations of a monosaccharide, oligosaccharide, polysaccharide and glycerin are from 0.1 to 30% (w/v); the preferable concentration of citric acid is from 0.01 to 10% (w/v); the preferable concentrations of ammonium sulfate, urea and amino acid are from 0.01 to 1% (w/v); and the preferable concentration of an inorganic substance is from 0.0001 to 0.5% (w/v). To the culture solution, the spore suspension is inoculated. The culture solution is cultured for preferably from 24 to 120 hours and more preferably from 48 to 72 hours, while stirring at preferably from 80 to 250 rpm and more preferably from 100 to 170 rpm and controlling a culture temperature to be from 25 to 42.5° C. The amount of the culture solution to be subjected to culture, which may be appropriately controlled depending upon the size of the culture vessel; may be, about from 50 to 100 mL, in the case of e.g., a 200 mL flask with a baffle, and about from 100 to 300 mL in the case of a 500 mL flask with a baffle. Owing to the culture, the spores inoculated are germinated and grow into mycelia.

<Step B2: Growth of Mycelium>

In view of improvement of C4 dicarboxylic acid productivity, it is preferable to perform a step (step B2) of proliferating the mycelium obtained in step B1 by further cultivation. The culture solution for proliferation to be used in step B2 is not particularly limited and may be sufficient if it is an inorganic culture solution routinely used and containing glucose; for example, a culture solution containing from 7.5 to 30% of glucose, from 0.05 to 0.2% of ammonium sulfate, from 0.03 to 0.6% of potassium dihydrogen phosphate, from 0.01 to 0.1% of magnesium sulfate heptahydrate, from 0.005 to 0.05% of zinc sulfate heptahydrate and from 3.75 to 20% of calcium carbonate (concentrations are all expressed by % (w/v)), may be mentioned. The amount of culture solution may be appropriately controlled depending upon the size of a culture vessel. For example, in the case of a 500 mL Erlenmeyer flask, the amount of culture solution may be sufficient if it is from 50 to 300 mL and preferably from 100 to 200 mL. To the culture solution, a mycelia cultured in step B1 was inoculated so as to obtain a rate of, as wet weight, from 1 to 6 g of mycelia/100 mL (culture solution) and preferably from 3 to 4 g of mycelia/100 mL (culture solution), and cultured for from 12 to 120 hours and preferably from 24 to 72 hours while stirring at from 100 to 300 rpm and preferably from 170 to 230 rpm and controlling a culture temperature to be from 25 to 42.5° C.

<Step C: Production of a C4 Dicarboxylic Acid>

The mycelium of a filamentous fungus obtained in the aforementioned procedure (step B1 or B2) is cultured to allow the fungus to produce a C4 dicarboxylic acid. The conditions of the cultivation may follow the culture conditions mentioned above and routinely used for filamentous fungi. The amount of medium can be about from 20 to 80 mL in the case of a 200 mL Erlenmeyer flask, about from 50 to 200 mL in the case of a 500 mL Erlenmeyer flask and about from 10 L to 15 L in the case of a 30 L jar fermenter; however, the amount of medium may be appropriately controlled depending upon the size of the culture vessel. The inoculation amount of the mycelium obtained in step B1 or B2 to the medium can be preferably, as wet weight, from 5 g to 90 g of mycelia/100 mL (medium) and more preferably from 5 g to 50 g of mycelia/100 mL (medium). Culture is preferably performed at a temperature of from 25 to 45° C. for from 2 hours to 240 hours and preferably from 12 hours to 120 hours while stirring at from 100 to 300 rpm and preferably from 150 to 230 rpm. If a jar fermenter is used, aeration is preferably performed at from 0.05 to 2 vvm and more preferably from 0.1 to 1.5 vvm.

The transformed cell of the present invention is cultured in the above procedure to produce a C4 dicarboxylic acid. After cultivation, the C4 dicarboxylic acid is recovered from the cultured broth. If necessary, the C4 dicarboxylic acid recovered may be further purified. A method for recovering or purifying a C4 dicarboxylic acid from the cultured broth is not particularly limited and may be performed in accordance with a recovery or purification method known in the art. For example, the C4 dicarboxylic acid in the cultured broth can be recovered or purified by removing cells and the like from a culture by a method such as a gradient method, filtration and centrifugation, if necessary concentrating the remaining culture, and subjecting the concentrate to a method such as a crystallization method, an ion exchange method and a solvent extraction method or a combination of these.

The transformed cell of the present invention separated from the cultured broth can be reused in producing a C4 dicarboxylic acid. For example, to the transformed cell of the present invention separated from the cultured broth, the medium as mentioned above is newly added. The mixture is cultured again in the aforementioned conditions to produce a C4 dicarboxylic acid. Then the C4 dicarboxylic acid produced can be recovered from the medium. This process can be further repeated. In the production method of the present invention, culturing a transformed cell and recovering a C4 dicarboxylic acid can be performed either one of a batch, semi-batch and continuous process.

4. Illustrative Embodiments

As an illustrative embodiment of the present invention, the following substances, production method, use and method will be further disclosed herein. However, the present invention is not limited to these embodiments.

[1] A polypeptide consisting of an amino acid sequence represented by SEQ ID No: 2 or an amino acid sequence having an identity of at least 90% with the amino acid sequence represented by SEQ ID No: 2.

[2] Preferably, the polypeptide according to [1], in which the amino acid sequence having an identity of at least 90% with the amino acid sequence represented by SEQ ID No: 2 is an amino acid sequence having an identity of 90% or more, preferably 95% or more, more preferably 96% or more, further preferably 97% or more, still further preferably 98% or more, and further more preferably 99% or more with the amino acid sequence represented by SEQ ID No: 2; or an amino acid sequence having deletion, substitution, addition or insertion of 1 or more and 10 or less, preferably 1 or more and 8 or less, more preferably 1 or more and 5 or less, and further preferably 1 or more and 3 or less amino acid(s), in the amino acid sequence represented by SEQ ID No: 2.

[3] Preferably, the polypeptide according to [1] or [2], being a multiple transmembrane polypeptide having three transmembrane helix structures and more preferably, a multiple transmembrane polypeptide having transmembrane helix structures in each of the corresponding regions to the 24th to 46th, 118th to 140th and 147th to 165th amino acid regions of the amino acid sequence represented by SEQ ID No: 2.

[4] Preferably, the polypeptide according to any one of [1] to [3], having a function to improve C4 dicarboxylic acid productivity in a cell.

[5] The polypeptide according to [4], in which the C4 dicarboxylic acid productivity in a cell is improved by preferably 10% or more, more preferably 15% or more, further preferably 20% or more, still further preferably 25% or more and further more preferably 30% or more.

[6] A polynucleotide encoding the polypeptide according to any one of [1] to [5].

[7] Preferably, the polynucleotide according to [6], consisting of a nucleotide sequence represented by SEQ ID No: 1 or a nucleotide sequence having an identity of at least 90% with the nucleotide sequence represented by SEQ ID No: 1.

[8] Preferably, the polynucleotide according to [7], in which the nucleotide sequence having an identity of at least 90% with the nucleotide sequence represented by SEQ ID No: 1, is a nucleotide sequence having an identity of 90% or more, preferably 95% or more, more preferably 96% or more, further preferably 97% or more, still further preferably 98% or more, further more preferably 99% or more with the nucleotide sequence represented by SEQ ID No: 1; or a nucleotide sequence having deletion, substitution, addition or insertion of 1 or more and 30 or less, preferably 1 or more and 24 or less, more preferably 1 or more and 15 or less and further preferably 1 or more and 9 or less nucleotide(s), with respect to the nucleotide sequence represented by SEQ ID No: 1.

[9] Preferably, the polynucleotide according to any one of [6] to [8], being cDNA or chemical synthesized DNA.

[10] A vector containing the polynucleotide according to any one of [6] to [9].

[11] Preferably, the vector according to [10], further containing a regulatory region operably linked to the polynucleotide.
[12] A DNA fragment containing the polynucleotide according to any one of [6] to [9].
[13] Preferably, the DNA fragment according to [12], further containing a regulatory region operably linked to the polynucleotide.
[14] A transformed cell containing the exogenous polynucleotide according to any one of [6] to [9].
[15] Preferably, the transformed cell according to [14], containing the vector according to [10] or [11] or a DNA fragment according to [12] or [13].
[16] The transformed cell according to [14] or [15], in which the cell is preferably a cell of a microbe.
[17] The transformed cell according to [16], in which the microbe is preferably a filamentous fungus.
[18] The transformed cell according to [17], in which the above filamentous fungus is preferably *Rhizopus*.
[19] The transformed cell according to [18], in which *Rhizopus* is preferably *Rhizopus delemar* or *Rhizopus oryzae* and more preferably *Rhizopus delemar*.
[20] The transformed cell according to any one of [14] to [19], in which C4 dicarboxylic acid productivity is preferably improved.
[21] The transformed cell according to [20], in which the dicarboxylic acid productivity is improved by preferably 10% or more, more preferably 15% or more, further preferably 20% or more, still further preferably 25% or more and further more preferably 30% or more.
[22] The transformed cell according to [20] or [21], in which the C4 dicarboxylic acid is preferably fumaric acid, malic acid or succinic acid.
[23] A method for producing a C4 dicarboxylic acid, comprising culturing the transformed cell according to any one of [14] to [22].
[24] The production method according to [23], preferably further comprising recovering a C4 dicarboxylic acid from the above cultured broth.
[25] The production method according to [23] or [24], in which the C4 dicarboxylic acid is preferably fumaric acid, malic acid or succinic acid.
[26] A method for producing a transformed cell, comprising introducing the polynucleotide according to any one of [6] to [9] into a host cell.
[27] A method for improving C4 dicarboxylic acid productivity in a host cell, comprising introducing the polynucleotide according to any one of [6] to [9] into the host cell.
[28] The method according to [27], in which the C4 dicarboxylic acid productivity in a host cell is improved by preferably 10% or more, more preferably 15% or more, further preferably 20% or more, still further preferably 25% or more and further more preferably 30%; or more.
[29] The method according to [27] or [28], in which the C4 dicarboxylic acid is preferably fumaric acid, malic acid or succinic acid.
[30] The method according to any one of [26] to [29], preferably comprising introducing the vector according to [10] or [11] or a DNA fragment according to [12] or [13] into a host cell.
[31] The method according to any one of [26] to [30], in which the host cell is preferably a cell of a microbe.
[32] The method according to [31], in which the microbe is preferably a filamentous fungus.
[33] The method according to [32], in which the filamentous fungus is preferably *Rhizopus*.
[34] The method according to [33], in which *Rhizopus* is preferably *Rhizopus delemar* or *Rhizopus oryzae* and more preferably *Rhizopus delemar*.

EXAMPLES

The present invention will be more specifically described below based on Examples; however, the present invention is not limited to these.

Example 1 Production of Transformed Cell (1) Genome Extraction

To PDA medium, spores of *Rhizopus delemar* JCM (Japan Collection of Microorganisms/Riken) 5557 strain (hereinafter referred to as 5557 strain) were inoculated and cultured at 30° C. for 5 days. After completion of the culture, mycelia were placed together with metal cones for a 3 mL tube (Yasui Kikai Corporation) in a 3 mL crushing tube and immediately frozen in liquid nitrogen for 10 minutes or more. Thereafter, the mycelia were crushed using a multi bead shocker (Yasui Kikai Corporation) at 1,700 rpm for 10 seconds. After completion of the crushing, 400 µL of TE Buffer (pH8.0) (Nippon Gene Co., Ltd.) was added to the container and mixed by turning the container upside down, and then, 250 µL of an aliquot was taken and transferred to a 1.5 mL tube. From the mycelium solution, a genome was extracted using "Dr. GenTLE (for yeast)" (Takara Bio Inc.) in accordance with the protocol. To 50 µL of the resultant genome solution, 1 µL of RNaseA (Roche) was added and allowed to react at 37° C. for one hour. After completion of the reaction, an equivalent amount of phenol chloroform was added and mixed by tapping. The mixture was centrifuged at 4° C. and 14,500 rpm for 5 minutes. The supernatant was transferred to a new 1.5 mL tube. The treatment with phenol chloroform was repeated and then precipitation with ethanol was performed to obtain a solution of purified genome of 5557 strain.

(2) Preparation of cDNA (i) Extraction of Total RNA 6 g, in wet weight, of mycelia of 5557 strain was inoculated in 40 mL of liquid medium (1 g/L $(NH_4)_2SO_4$, 0.6 g/L $KH_2PO_4$, 0.25 g/L $Mg_4SO_4.7H_2O$, 0.09 g/L $ZnSO_4.7H_2O$, 50 g/L calcium carbonate, 100 g/L glucose) and cultured at 35° C. and 170 rpm for 8 hours. Mycelia were recovered from the culture solution by filtration and washed twice with 100 mL of 0.85% physiological saline. After completion of the washing, extra water was removed by suction filtration. The mycelia (0.3 g) were weighed out, placed in a 3 mL crushing tube together with metal cones for a 3 mL tube (Yasui Kikai Corporation) and immediately placed in liquid nitrogen to freeze. The frozen mycelia thus obtained were crushed by a multi bead shocker (Yasui Kikai Corporation) at 1,700 rpm for 10 seconds. To the mycelia crushed, 500 µL of RLT buffer was added and mixed by turning the tube upside down, and then, 450 µL of an aliquot was subjected to RNeasy Plant Mini Kit (Qiagen) to extract total RNA. To 40 µL of the RNA solution thus obtained, 1 µL of DNaseI (TaKaRa) and 5 µL of 10× DNaseI buffer (USE Corporation) were added. The reaction solution was filled up to 50 µL with RNase free water and allowed to react at 37° C. for 30 minutes or more to remove residual DNA in the solution. DNaseI (1 µL) was further add to the solution, which was allowed to react at 37° C. for 30 minutes and then subjected to phenol/chloroform extraction, followed by ethanol precipitation. The precipitate was dissolved in 50 µL of sterilized water. The concentration and purity of the RNA solution were measured by Qubit (Life Technologies). The RNA solution was appropriately diluted and the RNA extracted was assayed by Agilent 2100 Bioanalyzer (Agilent) and RNA6000 Pico Kit (Agilent). The resultant RNA solution, which was confirmed to have an RNA decomposition index: "RNA Integrity Number (RIN value)" of 6.0 or more, was used as total RNA.

(ii) Synthesis of cDNA cDNA was synthesized using SuperScriptIII First-Strand Synthesis SuperMix for qRT-PCR (Invitrogen). More specifically, 1 µg of the RNA solution obtained in (i) was filled up to 8 µL with DEPC water. To the RNA solution, 10 µL of 2×RT Reaction Mix, and 2 µL of RT Enzyme Mix were added. The mixture was gently mixed and allowed to react at 25° C. for 10 minutes, 50° C. for 30 minutes and 85° C. for 5 minutes. After completion of the reaction, 1 µL of RNaseH was added to the solution and the mixture solution was allowed to react at 37° C. for 20 minutes and used as a cDNA solution.

(3) Preparation of Plasmid Vector (i) Introduction of trpC Gene Region in pUC18

Using the genomic DNA of 5557 strain obtained in (1) in the above, as a template, a DNA fragment containing a trpC gene (SEQ ID No: 3) was synthesized by PCR using primers oJK162 (SEQ ID No: 4) and oJK163 (SEQ ID No: 5). Subsequently, using plasmid pUC18 as a template, a DNA fragment was amplified by PCR using primers oJK164 (SEQ ID No: 6) and oJK165 (SEQ ID No: 7). The two fragments obtained above were ligated by In-Fusion HD Cloning Kit (Clontech) to construct plasmid pUC18-trpC.

(ii) Cloning of ADH1 Promoter and Terminator

Using the genomic DNA of 5557 strain obtained in (1) in the above, as a template, a DNA fragment containing a ADH1 promoter sequence (SEQ ID No: 8) and a DNA fragment containing a terminator sequence (SEQ ID No: 9) were amplified by PCR using a primer pair of oJK202 (SEQ ID No: 10) and oJK204 (SEQ ID No: 11) and a primer pair of oJK205 (SEQ ID No: 12) and oJK216 (SEQ ID No: 13), respectively. Subsequently, using plasmid pUC18-trpC obtained in (i) as a template, a DNA fragment was amplified by PCR using primer oJK210 (SEQ ID No: 14) and oJK211 (SEQ ID No: 15). The three fragments obtained above were ligated in the same manner as (i) to construct plasmid pUC18-trpC-Padh-Tadh. The plasmid thus obtained has ADH1 promoter and terminator arranged downstream of the trpC gene region in order. Further, a Not I restriction enzyme recognition sequence was arranged downstream of ADH1 terminator.

(iii) Preparation of Plasmid Vector

Using cDNA of 5557 strain obtained in (2) in the above, as a template, a DNA fragment containing a gene (hereinafter referred to as "rdt1") represented by SEQ ID No: 1 was amplified by PCR using primers oJK505 (SEQ ID No: 16) and oJK506 (SEQ ID No: 17). Subsequently, using plasmid pUC18-trpC-Padh-Tadh obtained in (ii), as a template, a DNA fragment was amplified by PCR using primers oJK204. (SEQ ID No: 11) and oJK269-4 (SEQ ID No: 18). The two fragments obtained above were ligated in the same procedure as in (i) to construct plasmid pUC18-trpC-Padh-rdt1-Tadh. The plasmid thus obtained has a rdt1 gene represented by SEQ ID No: 1 inserted between the ADH promoter and the terminator.

The PCR primers used in preparation of plasmid vector pUC18-trpC-Padh-rdt1-Tadh are shown in Table 1.

TABLE 1

| Primer | Sequence (5'→3') | SEQ ID No: |
|---|---|---|
| oJK162 | cgagctcgaattatttaaatgaacagcaagttaataatctagaggg | 4 |
| oJK163 | tatgaccatgattacgatgagaggcaaaatgaagcgtac | 5 |
| oJK164 | atttaaataattcgagctcggtacccgggg | 6 |
| oJK165 | cgtaatcatggtcatagctg | 7 |
| oJK202 | tagagggaaaaagagagaattgaaatagg | 10 |
| oJK204 | ttttgttatttaattgtattaattgataatg | 11 |
| oJK205 | aattaaataacaaaatcatttttaattacgcattttc | 12 |
| oJK216 | catgattacgcggccgcgccattataatgcactagtg | 13 |
| oJK210 | ctcttttccctctaatgagaggcaaaatgaagcgtac | 14 |
| oJK211 | aattaaataacaaaaatgtcttctatcgaaacctccaaaatctc | 15 |
| oJK505 | aattaaataacaaaaatgttacgtcctgtagaaaccccda | 16 |
| oJK506 | gcgtaattaaaatgattaatagaaaccctgcttaaatgcaagac | 17 |
| oJK269-4 | tcattttaattacgcattttcatttactaatttgttacattttgataacg | 18 |

(4) Introduction of Gene in Host Cell (i) Preparation of Tryptophan Auxotrophic Strain A tryptophan auxotrophic strain used as a host cell for gene introduction was selected from mutated strains which had been obtained by introducing a mutation to 5557 strain by ion beam irradiation. Ion beam irradiation was carried out at the ion irradiation facility of Takasaki Advanced Radiation Research Institute (TIARA: Takasaki Ion Accelerators for Advanced Radiation Application) of the Japan Atomic Energy Agency. Irradiation was carried out by accelerating $^{12}C^{5+}$ by using AVF cyclotron and applying 100 to 1,250 Gray at an energy of 220 MeV. Spores were recovered from the mycelia irradiated. From the spores, a tryptophan auxotrophic strain, *Rhizopus delemar* 02T6 strain (hereinafter, referred to as 02T6 strain) was obtained. 02T6 Strain has a deletion of a single base at 2093th position of the trpC gene coding region (SEQ ID No: 3) (full length: 2,298 bp).

(ii) Amplification of Plasmid Vector

*Escherichia coli* DH5 α strain (Nippon Gene Co., Ltd.) was transformed separately by plasmid vectors pUC18-trpC-Padh-Tadh and pUC18-trpC-Padh-rdt1-Tadh prepared in (3) in the above using a competent cell transformation method. Each of the transformed cells obtained were allowed to stand still at 37° C. overnight. The resultant colonies were inoculated in 2 mL of LBamp liquid medium (Bacto Trypton 1%, Yeast Extract 0.5%, NaCl 1%, ampicillin sodium 50 μg/mL) and cultured at 37° C. overnight. From the culture solution, each of the plasmid vectors was purified using a high pure plasmid isolation kit (Roche Life Science).

(iii) Introduction of Plasmid Vector in Host Cell

Each 10 μL of the DNA solutions (1 μg/μL) of plasmid vectors pUC18-trpC-Padh-Tadh and pUC18-trpC-Padh-rdt1-Tadh obtained in (ii) was added to 100 μL of a gold particle solution (60 mg/mL), followed by mixing. Thereafter, 40 μL of 0.1 M spermidine was added to the solution mixture and sufficiently stirred by a vortex. Further, 100 μL of 2.5M $CaCl_2$ was added to the solution mixture and stirred for one minute by a vortex, then centrifuged at 6,000 rpm for 30 seconds and the supernatant was removed. To the resultant precipitate, 200 μL of 70% EtOH was added. The solution was stirred for 30 seconds by a vortex and centrifuged at 6,000 rpm for 30 seconds and the supernatant was removed. The resultant precipitate was resuspended in 100 μL of 100% EtOH.

Subsequently, to the spores of 02T6 strain prepared in (i), a gene was introduced by GDS-80 (Nepa Gene Co., Ltd.) using the DNA-gold particle solution in the above. The spores having the gene introduced therein were subjected to stationary culture in an inorganic agar medium (20 g/L glucose, 1 g/L ammonium sulfate, 0.6 g/L potassium dihydrogen phosphate, 0.25 g/L magnesium sulfate heptahydrate, 0.09 g/L zinc sulfate heptahydrate, 15 g/L agar) at 30° C. for about a week. The mycelia grown were partly scraped off by a platinum loop and suspended in TE (pH8.0) (Nippon Gene Co., Ltd.). The suspension solution was treated at 95° C. for 15 minutes to extract a nucleic acid from transformed strains. A PCR reaction was carried out using the nucleic acid as a template and primers oJK438 (SEQ ID No: 19) and oJK439 (SEQ ID No: 20). The strain, which was confirmed to have a desired DNA fragment introduced therein, was selected as a transformed strain. The PCR primers are shown in Table 2. A strain in which pUC18-trpC-Padh-rdt1-Tadh containing DNA (where rdt1 gene is ligated downstream of ADH1 promoter) was introduced was designated as RDT1 strain. In contrast, a strain in which plasmid vector pUC18-trpC-Padh-Tadh containing DNA (where rdt1 gene is not inserted) was introduced was obtained as a negative control strain (hereinafter referred to as NC strain). The remaining mycelia were scraped off by a platinum loop and vigorously mixed in a spore recovery solution (8.5 g/L sodium chloride, 0.5 g/L polyoxyethylene sorbitan monooleate). After mixing, the spore suspension was filtered through a 3GP100 glass filter (cylindrical funnel) (SIBATA SCIENTIFIC TECHNOLOGY LTD.). The filtrate was used as a spore solution. The number of spores in the spore solution was measured by a hemocytometer (counting chamber, D=1/50 mm·1/400 $mm^2$).

TABLE 2

| Primer | Sequence (5'→3') | SEQ ID No: |
|---|---|---|
| oJK438 | gttccttgctgtggatttgtg | 19 |
| oJK439 | gggtgtatctctgtcctattcatg | 20 |

Example 2 Analysis of Transcript Amount of rdt1 Gene (1) Culture of Transformed Strain (i) Preparation of Mycelium A 500 mL Erlenmeyer flask with a baffle (Asahi Glass Co., Ltd.) was charged with 200 mL of SD/-Trp medium (Clontech) containing sorbitan monolaurate (Leodol SP-L10 (Kao Corp.)) in a final concentration of 0.5% (v/v). Each of the spore solutions of RDT1 strain and 5557 strain prepared in Example 1 was inoculated at a rate of $1×10^3$ spores/mL (medium) and then cultured at 27° C. for 3 days while stirring at 170 rpm. The resultant cultured broth was filtered through a stainless sieve (mesh size: 250 μm (AS ONE Corporation)) previously sterilized to recover mycelia on the filter.

(ii) Proliferation of Mycelium

To 100 mL of the inorganic culture solution (1 g/L $(NH_4)_2SO_4$, 0.6 g/L $KH_2PO_4$, 0.25 g/L $MgSO_4.7H_2O$, 0.09 g/L $ZnSO_4.7H_2O$, 50 g/L calcium carbonate, 100 g/L glucose) placed in a 500 mL Erlenmeyer flask, 5.0 to 8.0 g of the wet mycelia recovered in (i) was inoculated and cultured at 27° C. for about 40 hours, while stirring at 220 rpm. The resultant cultured broth was filtered by using a stainless screen filter holder (Millipore) previously sterilized to recover mycelia on the filter. The mycelia were further washed with 200 mL of physiological saline on the filter holder. The physiological saline used for washing was removed by suction filtration.

(2) Extraction of Total RNA

Each wet mycelia (6.0 g) of RDT1 strain and 5557 strain obtained in (1) in the above was inoculated in 40 mL of the inorganic culture solution for productivity evaluation (0.175 g/L $(NH_4)_2SO_4$, 0.06 g/L $KH_2PO_4$, 0.375 g/L $MgSO_4.7H_2O$, 0.135 g/L $ZnSO_4.7H_2O$, 50 g/L calcium carbonate, 100 g/L glucose) contained in a 200 mL Erlenmeyer flask and cultured at 35° C. for 8 hours while stirring at 170 rpm. From the culture solution, total RNA was extracted in the manner as described in Example 1(2)(i).

(3) Synthesis of cDNA

Using 500 ng of each total RNA of RDT1 strain and 5557 strain obtained in (2) in the above, cDNA was synthesized in accordance with the manner as described in Example 1(2)(ii).

(4) Real Time PCR Analysis

The transcript amount of rdt1 gene was analyzed using real time PCR analysis (Methods, 2001, 25 (4): 402-408). PCR reaction was carried out by using Brilliant III Ultra-Fast SYBR Green QPCR Master Mix (Agilent Technologies). As the primers for rdt1 gene, oJK862 (SEQ ID No: 21) and oJK863 (SEQ ID No: 22) were used. As the primers for a reference gene, actin2 gene, oJK869 (SEQ ID No: 23) and oJK870 (SEQ ID No: 24) were used. The sequences of the primers are shown in Table 3. The real time PCR analysis was carried out by using Stratagene Mx3005P (Agilent Technologies) (each strain n=12). The analysis results are shown in Table 4. In RDT1 strain, the transcript amount of rdt1 gene was improved up to 423%, compared to transcript amount (100%) of the rdt1 gene in a wild type strain, 5557 strain.

TABLE 3

| Primer | Sequence (5'→3') | SEQ ID No: |
|---|---|---|
| oJK862 | tcctcgcttggttcttcact | 21 |
| oJK863 | aaatgcaagaccggcaatag | 22 |
| oJK869 | tgacattgcaggaagagacg | 23 |
| oJK870 | tcctttgctgggtttaatgc | 24 |

TABLE 4

| Sample | Δct (Average, n = 12) | ΔΔct | Relative comparison |
|---|---|---|---|
| 5557 strain | −7.105 | −2.081 | 100% |
| RDT1 strain | −9.187 | | 423% |

Example 3 C4 Dicarboxylic Acid Productivity of RDT1 Strain (1) Culture of Transformed Strain (i) Preparation of Mycelium To a 200 mL of SD/-Trp medium (20 g/L glucose, 6.7 g/L Yeast nitrogen base w/o amino acids (Difco), 0.03 g/L L-Isoleucine, 0.15 g/L L-Valine, 0.02 g/L Adenine Hemisulfate Solt, 0.02 g/L L-Arginine HCl, 0.02 g/L L-Histidine HCl Monohydrate, 0.1 g/L L-Leucine, 0.03 g/L L-Lysine HCl, 0.02 g/L L-Methionine, 0.05 g/L L-Phenylalanine, 0.2 g/L L-Threonine, 0.03 g/L L-Tyrosine, 0.02 g/L Uracil) containing sorbitan monolaurate (Leodol SP-L10 (Kao Corp.)) in a final concentration of 0.5% (v/v) and placed in a 500 mL Erlenmeyer flask with a baffle (Asahi Glass Co., ltd.), each of the spore solutions of RDT1 strain and NC strain prepared in Example 1 was inoculated so as to achieve 1×10³ spores/mL (medium). The medium was cultured at 27° C. for 3 days while stirring at 170 rpm. The resultant cultured broth was filtered through a stainless sieve (mesh size: 250 μm (AS ONE Corporation)) previously sterilized to recover mycelia on the filter.

(ii) Proliferation of Mycelium

The mycelia were allowed to proliferate in the same conditions as in Example 2 (1) (ii).

(2) Evaluation of C4 Dicarboxylic Acid Productivity of Transformed Strain

Each wet mycelia (6.0 g) of RDT1 strain and NC strain obtained in (1) in the above was inoculated in 40 mL of an inorganic culture solution for productivity evaluation (0.175 g/L (NH$_4$)$_2$SO$_4$, 0.06 g/L KH$_2$PO$_4$, 0.375 g/L MgSO$_4$.7H$_2$O, 0.135 g/L ZnSO$_7$.7H$_2$O, 50 g/L calcium carbonate, 100 g/L glucose) placed in a 200 mL Erlenmeyer flask and cultured at 35° C. while stirring at 170 rpm. After culture for 54 hours, the culture supernatant containing no mycelia was recovered. Fumaric acid, malic acid, succinic acid and glucose were quantified in accordance with the procedure described later in Reference Example 1 and conversion rates (yield) of C4 dicarboxylic acids from glucose were calculated. Based on the obtained conversion rates in RDT1 strain and NC strain, the productivity improvement rates of individual C4 dicarboxylic acids in RDT1 strain were calculated in accordance with the following expression.

Improvement rate (%)=(conversion rate in RDT1 strain/conversion rate in NC strain)×100−100

The results are shown in Table 5. In RDT1 strain, productivity of malic acid was improved by 32.1%, fumaric acid by 57. 2% and succinic acid by 81.8%, compared to the respective productivity in NC strain having no rdt1 gene introduced therein.

TABLE 5

| Conversion rate from glucose (%; mean ± SD, n = 2) | | | |
|---|---|---|---|
| Name of strain | Malic acid | Fumaric acid conversion rate | Succinic acid conversion rate |
| RDT1 strain | 3.7 ± 0.09 | 33.8 ± 0.61 | 2.0 ± 0.07 |
| NC strain | 2.8 ± 0.09 | 21.5 ± 1.74 | 1.1 ± 0.06 |
| Productivity improvement rate (%) | | | |
| Name of strain | Malic acid | Fumaric acid | Succinic acid |
| RDT1 strain | 32.1 | 57.2 | 81.8 |

Reference Example 1 Quantification of C4 Dicarboxylic Acid and Glucose

C4 dicarboxylic acids (fumaric acid, malic acid and succinic acid) and glucose in a culture supernatant were quantified by HPLC.

The culture supernatant to be subjected to HPLC analysis was appropriately diluted in advance with 37 mM sulfuric acid. Insoluble matter was removed by DISMIC-13cp (0.20 μm cellulose acetate membrane, ADVANTEC) or AcroPrep 96 filter plate (0.2 μm GHP membrane, Pall Corporation).

As the HPLC apparatus, LaChrom Elite (Hitachi High-Technologies Corporation) was used. As the analysis column, a polymer column for organic acid analysis, ICSep ICE-ION-300 (7.8 mm I.D.×30 cm, TRANSGENOMIC) to which ICSep ICE-ION-300 Guard Column Cartridge (4.0 mm I.D.×2.0 cm, TRANSGENOMIC) was connected, was used. As the eluent, 10 mM sulfuric acid was used. Elution was carried out at a flow rate of 0.5 mL/minute and at a column temperature of 50° C. Each of C4 dicarboxylic acids and glucose were detected using a UV detector (detection wavelength 210 nm) and a differential refractive index detector (RI detector). Concentration calibration curves were prepared by using standard samples [fumaric acid (distributor code 063-00655, Wako Pure Chemical Industries, Ltd.), malic acid (distributor code 135-00562, Wako Pure Chemical Industries, Ltd.), succinic acid (distributor code 194-04335, Wako Pure Chemical Industries, Ltd.) and glucose (distributor code 045-31162, Wako Pure Chemical Industries, Ltd.)]. Individual components were quantified based on respective concentration calibration curves.

The value obtained by subtracting the amount of glucose quantified in the medium from the initial amount of glucose in the medium is regarded as the amount of glucose consumed. The ratios (%) of individual C4 dicarboxylic acid amounts relative to the amount of glucose consumed were calculated and regarded as conversion rates (yield) of individual C4 dicarboxylic acids.

What is claimed is:

1. A method for producing a C4 dicarboxylic acid, comprising culturing a cell that has been transformed with:
   (a) a polynucleotide encoding a polypeptide consisting of the amino acid sequence of SEQ ID NO: 2, or a polypeptide that has an amino acid sequence having an identity of at least 90% with the amino acid sequence of SEQ ID NO: 2 and that has a plurality of transmembrane helix structures,
   or
   (b) a vector containing the polynucleotide,
   and producing the C4 dicarboxylic acid as a result of the culturing.

2. The method according to claim 1, wherein the amino acid sequence having an identity of at least 90% with the amino acid sequence of SEQ ID NO: 2 is an amino acid sequence having a deletion, substitution, addition or insertion of 1 or more and 10 or less amino acid(s) with respect to the amino acid sequence of SEQ ID NO: 2.

3. The method according to claim 1, wherein expression of the polypeptide improves C4 dicarboxylic acid productivity in a cell.

4. The method according to claim 1, wherein the polypeptide is encoded by a polynucleotide that has
   the nucleotide sequence of SEQ ID NO: 1 or
   a nucleotide sequence that has an identity of at least 90% with that of the nucleotide sequence of SEQ ID NO: 1.

5. The method according to claim 1, wherein the transformed cell is a cell of a microbe.

6. The method according to claim 5, wherein the microbe is a filamentous fungus.

7. The method according to claim 6, wherein the filamentous fungus is *Rhizopus*.

8. The method according to claim 7, wherein the *Rhizopus* is *Rhizopus delemar*.

9. The method according to claim 1, further comprising recovering the C4 dicarboxylic acid from broth in which the cell has been cultured.

10. The method according to claim 1, wherein the C4 dicarboxylic acid is fumaric acid, malic acid or succinic acid.

11. A transformed cell, wherein the cell has been transformed with:
   (a) a polynucleotide encoding a polypeptide consisting of the amino acid sequence of SEQ ID NO: 2, or a polypeptide that has an amino acid sequence having an identity of at least 90% with the amino acid sequence of SEQ ID NO: 2 and that has a plurality of transmembrane helix structures;
   or
   (b) a vector containing the polynucleotide.

12. The transformed cell according to claim 11, wherein the amino acid sequence having an identity of at least 90% with the amino acid sequence of SEQ ID NO: 2 is an amino acid sequence having a deletion, substitution, addition or insertion of 1 or more and 10 or less amino acid(s) with respect to the amino acid sequence of SEQ ID NO: 2.

13. The transformed cell according to claim 11, comprising a vector containing the polynucleotide.

14. The transformed cell according to claim 11, wherein the cell is a cell of a microbe.

15. The transformed cell according to claim 14, wherein the microbe is a filamentous fungus.

16. The transformed cell according to claim 15, wherein the filamentous fungus is *Rhizopus*.

17. The transformed cell according to claim 16, wherein *Rhizopus* is *Rhizopus delemar*.

18. An expression vector comprising a polynucleotide encoding:
   a polypeptide consisting of the amino acid sequence of SEQ ID NO:2 or
   an amino acid sequence having an identity of at least 90% with the amino acid sequence of SEQ ID NO:2 and that has a plurality of transmembrane helix structures.

19. The expression vector according to claim 18, wherein the amino acid sequence having an identity of at least 90% with the amino acid sequence of SEQ ID NO: 2 is an amino acid sequence having a deletion, substitution, addition or insertion of 1 or more and 10 or less amino acid(s) with respect to the amino acid sequence of SEQ ID NO: 2.

20. The method of claim 1, wherein the polynucleotide encodes a polypeptide consisting of the amino acid sequence of SEQ ID NO: 2.

21. The transformed cell of claim 11, wherein the cell has been transformed with a polynucleotide that encodes a polypeptide consisting of the amino acid sequence of SEQ ID NO: 2.

22. The vector of claim 18, wherein the vector comprises a polynucleotide encoding a polypeptide consisting of the amino acid sequence of SEQ ID NO:2.

23. The method of claim 1, wherein the polypeptide has a transmembrane helix structure in each of the regions corresponding to the $24^{th}$ to $46^{th}$, the $118^{th}$ to $140^{th}$ and the $147^{th}$ to $165^{th}$ amino acids of the amino acid sequence of SEQ ID NO:2.

24. The transformed cell of claim 11, wherein the polypeptide has a transmembrane helix structure in each of the regions corresponding to the $24^{th}$ to $46^{th}$, the $118^{th}$ to $140^{th}$ and the $147^{th}$ to $165^{th}$ amino acids of the amino acid sequence of SEQ ID NO:2.

25. The expression vector of claim 21, wherein the polypeptide has a transmembrane helix structure in each of the regions corresponding to the $24^{th}$ to $46^{th}$, the $118^{th}$ to $140^{th}$ and the $147^{th}$ to $165^{th}$ amino acids of the amino acid sequence of SEQ ID NO:2.

* * * * *

SEQUENCE LISTING

<160> NUMBER OF SEQ ID NOS: 24

<210> SEQ ID NO 1
<211> LENGTH: 513
<212> TYPE: DNA
<213> ORGANISM: Rhizopus delemar

<400> SEQUENCE: 1

```
atgtcttcta tcgaaacctc caaaatctca agttttatga tcaacaatat tgatgacttt      60
gttgcagatt ggcatgttcg cgttacttgg atcgcattca tgacactctg ggtcttttgg     120
ggattggttt gggttttccg caacttcttt gtttcaaact ctcctgcatt gactcctgct     180
cctgaagcaa atgctgctga tgatacggaa gcatcaaaga aaaaactctt tagcgttacc     240
agtgacagtt ttgctcttcg tctagatcgt gctcatcaag ttgtaaaaga tgccttgttc     300
tctcttctct gtcttctttc catgaactcc tttgctcgtg cttcaactcg tgctgtcatg     360
atcctcgctt ggttcttcac tgcctttgct gtctgttggt ttgctgtcgt attccttgtt     420
gataaccgct ttgttcgttt gacgtattca cttgtctttt acgctcttgg tcttgctatt     480
gccggtcttg catttaagca gggtttctat taa                                  513
```

<210> SEQ ID NO 2
<211> LENGTH: 170
<212> TYPE: PRT
<213> ORGANISM: Rhizopus delemar

<400> SEQUENCE: 2

```
Met Ser Ser Ile Glu Thr Ser Lys Ile Ser Ser Phe Met Ile Asn Asn
 1               5                  10                  15

Ile Asp Asp Phe Val Ala Asp Trp His Val Arg Val Thr Trp Ile Ala
             20                  25                  30

Phe Met Thr Leu Trp Val Phe Trp Gly Leu Val Trp Val Phe Arg Asn
         35                  40                  45

Phe Phe Val Ser Asn Ser Pro Ala Leu Thr Pro Ala Pro Glu Ala Asn
     50                  55                  60

Ala Ala Asp Asp Thr Glu Ala Ser Lys Lys Lys Leu Phe Ser Val Thr
 65                  70                  75                  80

Ser Asp Ser Phe Ala Leu Arg Leu Asp Arg Ala His Gln Val Val Lys
                 85                  90                  95

Asp Ala Leu Phe Ser Leu Leu Cys Leu Leu Ser Met Asn Ser Phe Ala
            100                 105                 110

Arg Ala Ser Thr Arg Ala Val Met Ile Leu Ala Trp Phe Phe Thr Ala
        115                 120                 125

Phe Ala Val Cys Trp Phe Ala Val Val Phe Leu Val Asp Asn Arg Phe
    130                 135                 140

Val Arg Leu Thr Tyr Ser Leu Val Phe Tyr Ala Leu Gly Leu Ala Ile
145                 150                 155                 160

Ala Gly Leu Ala Phe Lys Gln Gly Phe Tyr
                165                 170
```

<210> SEQ ID NO 3
<211> LENGTH: 2298
<212> TYPE: DNA
<213> ORGANISM: Rhizopus delemar

<400> SEQUENCE: 3

```
atgaccactt tacttattga caactacgac agttttactt ataatgtcta tcaatacttg      60
```

-continued

| | |
|---|---|
| agctgccaag gcgccaatgt agttgtctac agaaacgaca aaatcaccat ttccgaaatt | 120 |
| gagcaattgg ctcctcgcaa tattgtcatc tcacctggcc ctggccaccc ttccaccgat | 180 |
| gccggtgtct ctcgagaggc cattcgagct tttgcaggaa agattcccat cttgggtatt | 240 |
| tgtatgggtc agcaatgtat gtatgaagtg tacggtggta aagtgtcata tgcaggtgat | 300 |
| attgtgcatg gcaaggcatc cagcatcaag catgacagtc gaggtatctt caagggcgtt | 360 |
| cctcaaaaca acatggtcac tcgttaccat tcccttgctg gcatgccttc tactttacct | 420 |
| gaaacattag aagtcactgc gactaccgac gatggtatca tcatgggcat cgacacaag | 480 |
| gaatacactg tcgaaggtgt tcagttccat cctgaaagta tcctttgtga acacggacat | 540 |
| acgatgatca acaacttctt aagcttgcgt ggtggcacct gggaagagaa tcctgcagcc | 600 |
| ggtgttgtct ttaagaaagc tcgttccgaa cacccaaaa tcagtgctag tgaatcccaa | 660 |
| ctcgatctct ctcagcaaca acctgccgca gcaccttcca tcttgacccg catttactct | 720 |
| caacgactca aggatgttca ggcagccaag gagattcccg ccagacatt tgaagattta | 780 |
| gaaaacttt taaagttgca cgtcgcccca cctcttcaag acgtcgtcgc tcgcgtgcgt | 840 |
| caaagcaagc ccgccttgat ggccgaagtc aagcgtgcct ctccctcgaa aggaaacatt | 900 |
| gatgtttcgg ccaacgcggc tgagcaggca cttcaatatg cttagcagg tgcaagcgtc | 960 |
| gtctctgttc tgactgaacc caaatggttc cgcggtacga ttcatgatat gcatcaggtc | 1020 |
| cgagaggcct tgagccatct gcccaaccgt ccttgtgtgt tgagaaagga ttttattgtc | 1080 |
| gatcgctatc aaatcttgga aggttgtctg tacggtgctg atactatctt gttgatcgtg | 1140 |
| gccatgctga atgatgaaca actgcacgaa ttgtatcact atgcgaaatc attaggtatg | 1200 |
| gaacccttgg tcgaagtcaa taatacggaa gagatggccc gtgccaatgc tttgggcgca | 1260 |
| cgtctggtgt gtgttaataa tcgcaacttg cacagctttg atgttgatat ggaaaccacg | 1320 |
| agtcgattgg tagagatggt gcctgaagga acgatcttgt gtgcactttc tggtattact | 1380 |
| ggacgagctg atgttgaaat gtacgtcaaa cagggtgtgc acgctgtctt ggtgggtgaa | 1440 |
| gccctgatgc gtgcttggaa tttgaaggag tttgtgtctg atttgttggg tcatgaaaag | 1500 |
| aaggatcctg tgcctgtgtc caaggaatca aaatcttcac tagtcaaggt atgtggtatc | 1560 |
| tctagtgtgg atgcagcagt tgaagcagcc aagtcagggg ctgacttgat tggtcttatc | 1620 |
| tttgctgaaa agtccaaacg aaaagtgtct ttggaaagag ctcaagaaat cgtgtcctca | 1680 |
| gtgcgtgcgt tggatattca agtcaaacga acgttatcaa atgatgattc tcaactggat | 1740 |
| tggttccaga tgcacaagcg tctcttggaa aagcgagcaa gaaaaccttt ggtagttggc | 1800 |
| gtgtttgtga atcaatcgat tgaatacatg actgaggtgg caacgacagt cggactggac | 1860 |
| cttattcagc tgcatggaac cgaatcaacg gagcttgcac gctatttacc cgtgcctgtc | 1920 |
| atcaaagctt tccatatcga cagtggtgag ttcaatgaag ctcagatacc aaacctaaat | 1980 |
| caaccaggct cttatcatta tgtcttactg gacgctaaag tgcccagctt accatcggat | 2040 |
| caacaaggtg gacgtggtgt caagtttgat tggtcaattg ctaccaaaat cgtgaaacat | 2100 |
| aggcactttg agttttttggg taatcaagat ttccctgtca tcttggctgg tgggttggat | 2160 |
| cctaccaatg tggcatctgc cattcaacag gtgaaaccct ggattgtgga tgtgtcgagt | 2220 |
| ggtgttgaaa cagatggagt gaaggattta gaaaagattc gtgcctttgt taaaactgtc | 2280 |
| cagtcaacac aattttaa | 2298 |

<210> SEQ ID NO 4
<211> LENGTH: 46

```
<212> TYPE: DNA
<213> ORGANISM: Artificial
<220> FEATURE:
<223> OTHER INFORMATION: Synthetic oligonucleotide

<400> SEQUENCE: 4
cgagctcgaa ttatttaaat gaacagcaag ttaataatct agaggg             46

<210> SEQ ID NO 5
<211> LENGTH: 39
<212> TYPE: DNA
<213> ORGANISM: Artificial
<220> FEATURE:
<223> OTHER INFORMATION: Synthetic oligonucleotide

<400> SEQUENCE: 5
tatgaccatg attacgatga gaggcaaaat gaagcgtac                     39

<210> SEQ ID NO 6
<211> LENGTH: 30
<212> TYPE: DNA
<213> ORGANISM: Artificial
<220> FEATURE:
<223> OTHER INFORMATION: Synthetic oligonucleotide

<400> SEQUENCE: 6
atttaaataa ttcgagctcg gtacccgggg                               30

<210> SEQ ID NO 7
<211> LENGTH: 20
<212> TYPE: DNA
<213> ORGANISM: Artificial
<220> FEATURE:
<223> OTHER INFORMATION: Synthetic oligonucleotide

<400> SEQUENCE: 7
cgtaatcatg gtcatagctg                                          20

<210> SEQ ID NO 8
<211> LENGTH: 1000
<212> TYPE: DNA
<213> ORGANISM: Rhizopus delemar

<400> SEQUENCE: 8
tagagggaaa aagagagaat tgaaatagga gaggatgagt caaaatatag tttacataaa    60
atttctcttt tttgtgttaa atataatcta atagcagggg ttttcttagt ttacgtttat   120
atcaaagtta tcaagcatac acttttttat gattttcat  actttaatcc cttttagtat   180
tctattgttt gaaaggagag aaaaaacagc tgagggtacg gtgcacacga gatcttacga   240
taattttcct gcccaacagg aaagaagtaa ttgatcttga ttgacgctcg gagtttgcac   300
gttcggagtt tgcacttcac attgagttat actcttactt attttgaagg aagggacgag   360
aaaagatgta aatataataa taacagtagt aaatagtatg cgcatcaaga acagctacca   420
acaaaagaga gaaatatgag cttaataatg aacaatgtaa atggcagaat gaaatttaat   480
tatcaaagcg gcatctttca gaccttccgt tacttccgat agagttttttt atgcaaagta   540 ataacaactg tatatataaa aaaaagaagg ttatcaagca aaagccacaa tgtcatatct   600
ggaataatca agagtaacta ttgaatgttg gtagccaaaa gaggcacgta atttttatgac   660 gaaatatcac acaaaaagat tattttgaca attcatgaat aggacagaga tacaccctaa   720
acatgaaatg taagctatat ttaaacacct caagttaatt ttgaagcttc atttgtatta   780
```

```
ttgtaaccat ttagacaagc taaatccttt ttattattgt ccttattgat tttatccaga      840
ttaccgtatc taaagagcga tcaacagaaa aacggctgat tttagaccaa agtttcacaa      900
actacatttg catgaacgtc atatatatat aaaccttgac ttttctttt tttttttttt      960 ttttttttc attatcaatt aatacaatta aataacaaaa                           1000
```

<210> SEQ ID NO 9
<211> LENGTH: 634
<212> TYPE: DNA
<213> ORGANISM: Rhizopus delemar

<400> SEQUENCE: 9

```
tcattttaat tacgcatttt catttactaa tttgttacat tttgataacg tcaataaatc       60
ttctaatttc ttttgttctc aaacagtttta cagttctatc ttttttttta ccacaatcaa     120
ttctcaatat acaacatagc aaatgtgctt cagtaaattc attaaattct tttaaaaaaa     180
ggtaatttgt agcataaaat tcgactttat tgacgttttt tttatgatca tatacaaata     240
aaatagttgc gaatgagaac taaattttc attgttttta gtcatatcat ctggctgttg      300
cacgatgatc gcagcatatt tttcttcaca acactcatcc tataagcacc tttcaggact     360
ttcgtctgca ctttccatat ttgatttcat caattgattt gaattttttat ccagtacaat    420 ggtttgaatc tatacaataa attagtcaca gtataaaatt atgtctcatc ttgaacacac     480
acctgcttaa caaagaaatg aagcactcta tcaatagtaa atacaatata tgcatcgatg    540
ccaaatatat atcgtacatt ctcttcaaac gtagcttgat ctaaatcgcc atcaataaac    600
ctttcaatca tcctcactag tgcattataa tggc                                634
```

<210> SEQ ID NO 10
<211> LENGTH: 29
<212> TYPE: DNA
<213> ORGANISM: Artificial
<220> FEATURE:
<223> OTHER INFORMATION: Synthetic oligonucleotide

<400> SEQUENCE: 10

```
tagagggaaa aagagagaat tgaaatagg                                         29
```

<210> SEQ ID NO 11
<211> LENGTH: 31
<212> TYPE: DNA
<213> ORGANISM: Artificial
<220> FEATURE:
<223> OTHER INFORMATION: Synthetic oligonucleotide

<400> SEQUENCE: 11

```
ttttgttatt taattgtatt aattgataat g                                      31
```

<210> SEQ ID NO 12
<211> LENGTH: 36
<212> TYPE: DNA
<213> ORGANISM: Artificial
<220> FEATURE:
<223> OTHER INFORMATION: Synthetic oligonucleotide

<400> SEQUENCE: 12

```
aattaaataa caaaatcatt ttaattacgc attttc                                 36
```

<210> SEQ ID NO 13
<211> LENGTH: 37
<212> TYPE: DNA
<213> ORGANISM: Artificial

```
<220> FEATURE:
<223> OTHER INFORMATION: Synthetic oligonucleotide

<400> SEQUENCE: 13
catgattacg cggccgcgcc attataatgc actagtg                               37

<210> SEQ ID NO 14
<211> LENGTH: 38
<212> TYPE: DNA
<213> ORGANISM: Artificial
<220> FEATURE:
<223> OTHER INFORMATION: Synthetic oligonucleotide

<400> SEQUENCE: 14 ctcttttttcc ctctaatgag aggcaaaatg aagcgtac                             38

<210> SEQ ID NO 15
<211> LENGTH: 44
<212> TYPE: DNA
<213> ORGANISM: Artificial
<220> FEATURE:
<223> OTHER INFORMATION: Synthetic oligonucleotide

<400> SEQUENCE: 15
aattaaataa caaaaatgtc ttctatcgaa acctccaaaa tctc                       44

<210> SEQ ID NO 16
<211> LENGTH: 39
<212> TYPE: DNA
<213> ORGANISM: Artificial
<220> FEATURE:
<223> OTHER INFORMATION: Synthetic oligonucleotide

<400> SEQUENCE: 16
aattaaataa caaaaatgtt acgtcctgta gaaaccccca                            39

<210> SEQ ID NO 17
<211> LENGTH: 44
<212> TYPE: DNA
<213> ORGANISM: Artificial
<220> FEATURE:
<223> OTHER INFORMATION: Synthetic oligonucleotide

<400> SEQUENCE: 17
gcgtaattaa aatgattaat agaaaccctg cttaaatgca agac                       44

<210> SEQ ID NO 18
<211> LENGTH: 50
<212> TYPE: DNA
<213> ORGANISM: Artificial
<220> FEATURE:
<223> OTHER INFORMATION: Synthetic oligonucleotide

<400> SEQUENCE: 18
tcattttaat tacgcatttt catttactaa tttgttacat tttgataacg                 50

<210> SEQ ID NO 19
<211> LENGTH: 21
<212> TYPE: DNA
<213> ORGANISM: Artificial
<220> FEATURE:
<223> OTHER INFORMATION: Synthetic oligonucleotide

<400> SEQUENCE: 19
gttccttgct gtggatttgt g                                                21
```

```
<210> SEQ ID NO 20
<211> LENGTH: 24
<212> TYPE: DNA
<213> ORGANISM: Artificial
<220> FEATURE:
<223> OTHER INFORMATION: Synthetic oligonucleotide

<400> SEQUENCE: 20
gggtgtatct ctgtcctatt catg                                          24

<210> SEQ ID NO 21
<211> LENGTH: 20
<212> TYPE: DNA
<213> ORGANISM: Artificial
<220> FEATURE:
<223> OTHER INFORMATION: Synthetic oligonucleotide

<400> SEQUENCE: 21
tcctcgcttg gttcttcact                                               20

<210> SEQ ID NO 22
<211> LENGTH: 20
<212> TYPE: DNA
<213> ORGANISM: Artificial
<220> FEATURE:
<223> OTHER INFORMATION: Synthetic oligonucleotide

<400> SEQUENCE: 22
aaatgcaaga ccggcaatag                                               20

<210> SEQ ID NO 23
<211> LENGTH: 20
<212> TYPE: DNA
<213> ORGANISM: Artificial
<220> FEATURE:
<223> OTHER INFORMATION: Synthetic oligonucleotide

<400> SEQUENCE: 23
tgacattgca ggaagagacg                                               20

<210> SEQ ID NO 24
<211> LENGTH: 20
<212> TYPE: DNA
<213> ORGANISM: Artificial
<220> FEATURE:
<223> OTHER INFORMATION: Synthetic oligonucleotide

<400> SEQUENCE: 24
tcctttgctg ggtttaatgc                                               20
```